United States Patent [19]
Sen et al.

[11] Patent Number: 5,948,897
[45] Date of Patent: Sep. 7, 1999

[54] METHOD OF BINDING TWO OR MORE DNA DOUBLE HELICES AND PRODUCTS FORMED

[75] Inventors: Dipankar Sen; Eduard Antoni Venczel, both of Vancouver, Canada

[73] Assignee: Simon Fraser University, Canada

[21] Appl. No.: 08/874,319

[22] Filed: Jun. 13, 1997

Related U.S. Application Data

[60] Provisional application No. 60/019,795, Jun. 14, 1996.
[51] Int. Cl.[6] .......................... C07H 21/00; C07H 21/02; C07H 21/04; C12Q 1/68
[52] U.S. Cl. ...................... 536/22.1; 536/23.1; 536/24.3; 435/6
[58] Field of Search .................................. 536/23.1, 24.3, 536/22.1; 435/6

[56] References Cited

U.S. PATENT DOCUMENTS

| | | | |
|---|---|---|---|
| 5,624,803 | 4/1997 | Noonberg et al. | 435/6 |
| 5,674,683 | 10/1997 | Kool | 435/6 |

OTHER PUBLICATIONS

Sen et al., Nature 344 :410–414 (1990).
Sen et al., Nature 334 :364–366 (1988).
Sen et al., Methods in Enzymology 211 :191–199 (1992).
Amato, I. "Designer Solids: Haute Couture in Chemistry" *Science* vol. 260, May 7, 1993: pp. 753–755.
Chen, J.H. E Seeman, N.C. "Synthesis from DNA of a Molecule With the Connectivity of a Cube" *Nature* vol. 350, Apr. 18, 1991: pp. 631–633.
Duckett, D.R. et al. "The Structure of the Holliday Junction, and Its Resolution" *Cell* vol. 55, Oct. 7, 1988: pp. 79–89.
Duckett, D.R. E Lilley, D.M.J. "The three–way DNA junction is a Y–shaped molecule in which there is no helix–helix stacking" *EMBO Journal* vol. 9, 1990: pp. 1659–1664.
Lu, M. et al. "Structure and Stability of Sodium and Potassium Complexes of $dT_4G_4$ and $dT_4G_4T$" *Biochemistry* vol. 31, 1992: pp. 2455–2459.
Marsh, T.C. & Henderson, E. "G–Wires: Self–Assembly of a Telomeric Oligonucleotide, d(GGGGTTGGGG), into Large Superstructures" *Biochemistry* vol. 33, 1994: pp. 10718–10724.
Murphy, C.J. et al. "Long–Range Photoinduced Electron Transfer Through a DNA Helix" *Science* vol. 262, Nov. 12, 1993: pp. 1025–1029.
Seeman, N.C. et al. "DNA Nanoconstructions" *Journal Vacuum Science and Technology* vol. 12, Jul./Aug., 1994: pp. 1895–1903.
Sen, D. & Gilbert, W. "The Structure of Telomeric DNA: DNA Quadriplex Formation" *Current Opinion in Structural Biology I*, 1991: pp. 435–438.
Sen, D. & Gilbert W. "Novel DNA Superstructures Formed By Telomere–like Oligomers" *Biochemistry* vol. 31, No. 1, 1992: pp. 65–70.
Venczel, E.A. & Sen, D. "Parallel and Antiparallel G–DNA Structures from a Complex Telomeric Sequence" *Biochemistry* vol. 32, No. 24, 1993: pp. 6220–6228.
Wang, Y. et al. "Assembly and Characterization of Five–Arm and Six–Arm DNA Branched Junctions" *Biochemistry* vol. 30, N. 23, 1991: pp. 5667–5674.

*Primary Examiner*—W. Gary Jones
*Assistant Examiner*—Ethan C Whisenant
*Attorney, Agent, or Firm*—Hall, Priddy & Myers

[57] ABSTRACT

This invention relates to a nucleic acid complex having double-stranded sections with a domain of guanine nucleotides. The domain comprises of a pair of substantially uninterrupted guanine sequences which bond together. This domain can interact with other similar domains such that two nucleic acid complexes with these domains have the ability to bind together to form DNA superstructures. The present invention also relates to a method of forming a nucleic acid superstructure using the engineered nucleic acid complexes.

58 Claims, 10 Drawing Sheets

Duplex A.B

5' GTGACTCGAGAAGCTCCTGAGGGGGGGTGTGGTTCAAGGATCCACAG
   CACTGAGCTCTTCGAGGACTGGGGGGGGACACCAAGTTCCTAGGTGTC 5'

FIG. 5a

Duplex A'.B'

5' GTGACTCGAGAAGCTCCTGATTTTTGGGGGGGGTTTTTGTGGTTCAAGGATCCACAG
   CACTGAGCTCTTCGAGGACTTTTTTGGGGGGGTTTTTACACCAAGTTCCTAGGTGTC 5'

FIG. 5b

Duplex A.C

5' GTGACTCGAGAAGCTCCTGAGGGGGGGTGTGGTTCAAGGATCCACAG
                 3' AGCTCTTCGAGGACTGGGGGGGACACCAAGTTCCTAG

FIG. 5c

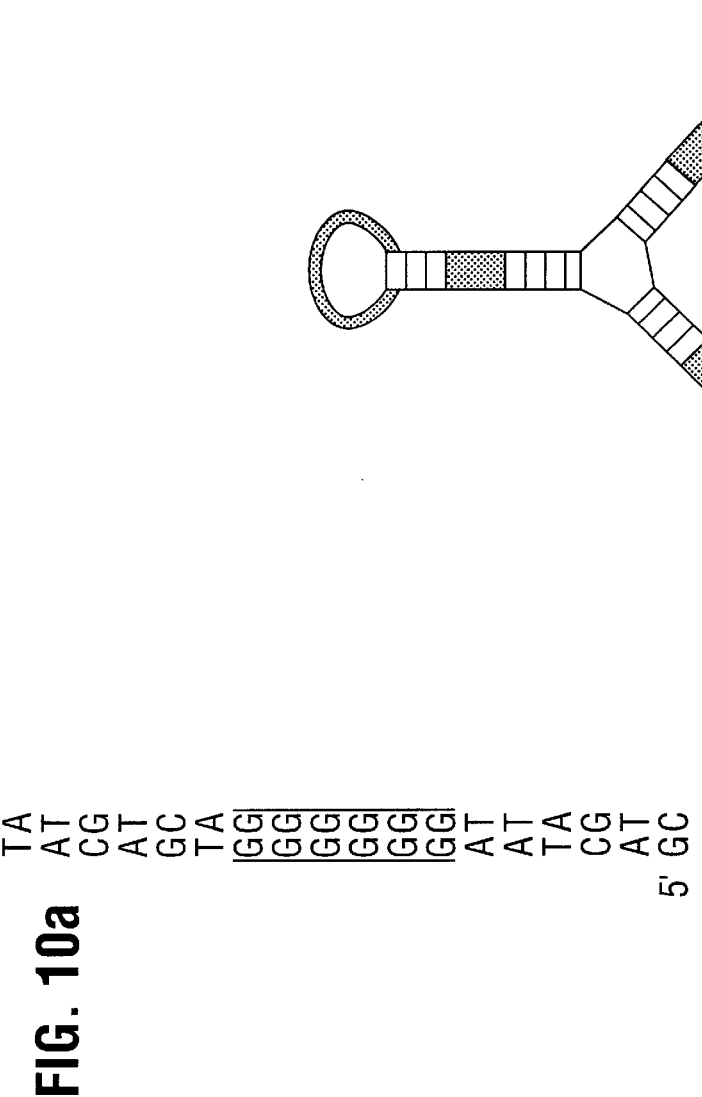
FIG. 10a
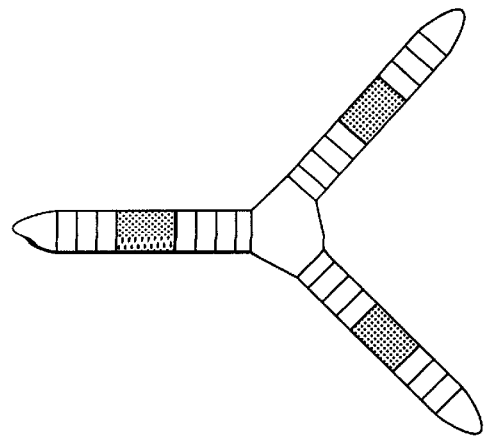
FIG. 10c
FIG. 10b

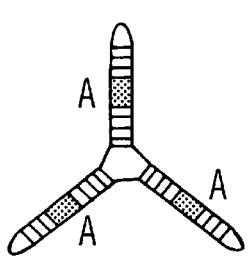 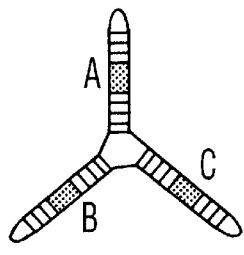 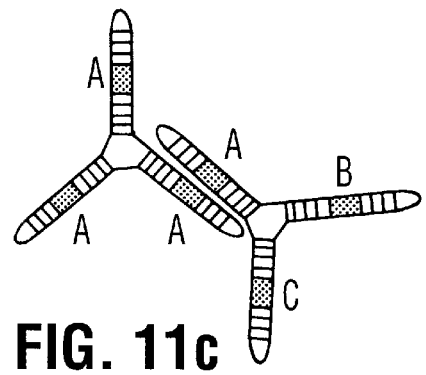
FIG. 11a  FIG. 11b  FIG. 11c
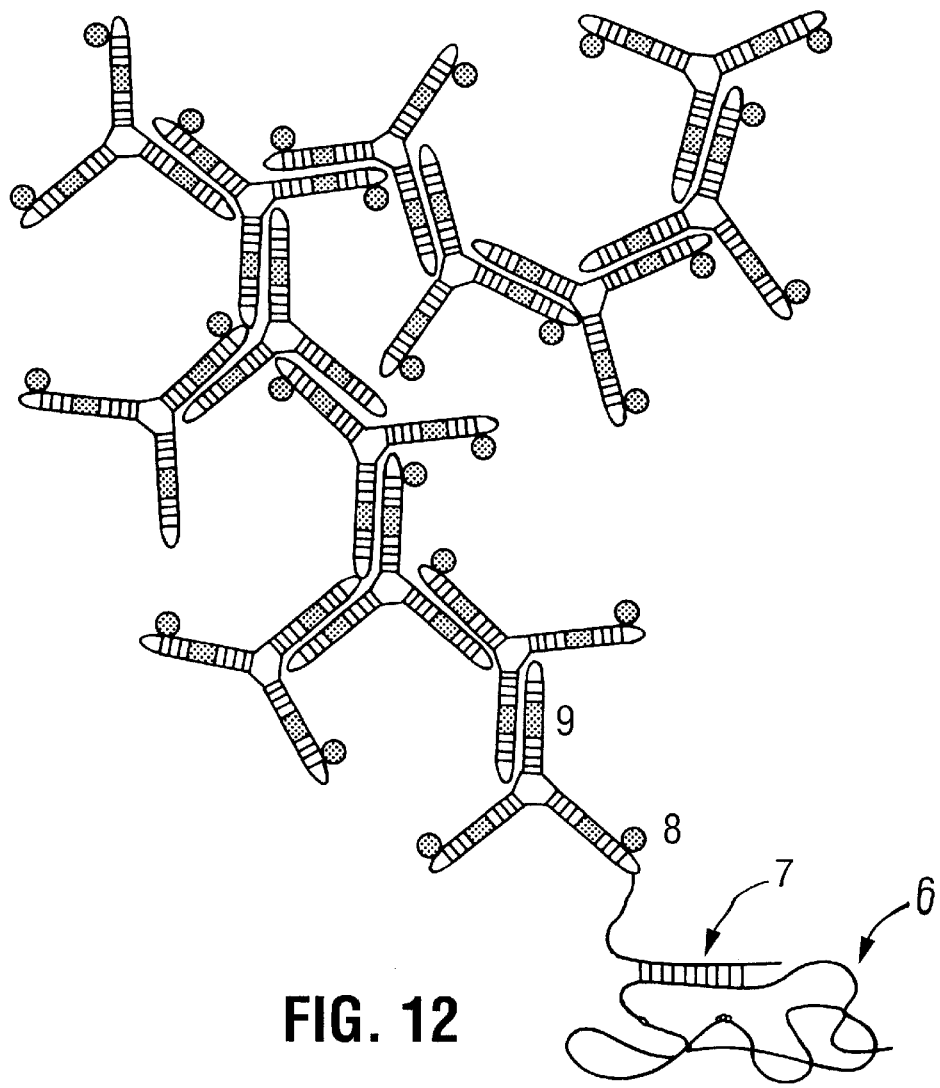
FIG. 12

```
5' ACTAGCTATAGCC GGGGGGGG TATACCAGATAC
   TGATCGATATCGG GGGGGGGG ATATGGTCTATG 5'
                T GGGGGGGG TATACCAGATAC
                T GGGGGGGG ATATGGTCTATG 5'
```

FIG. 13

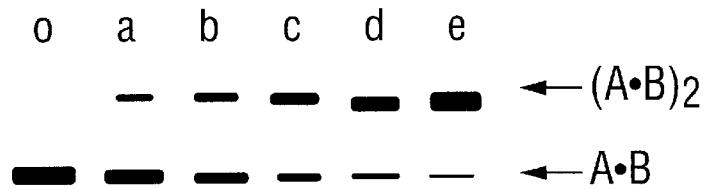
FIG. 14
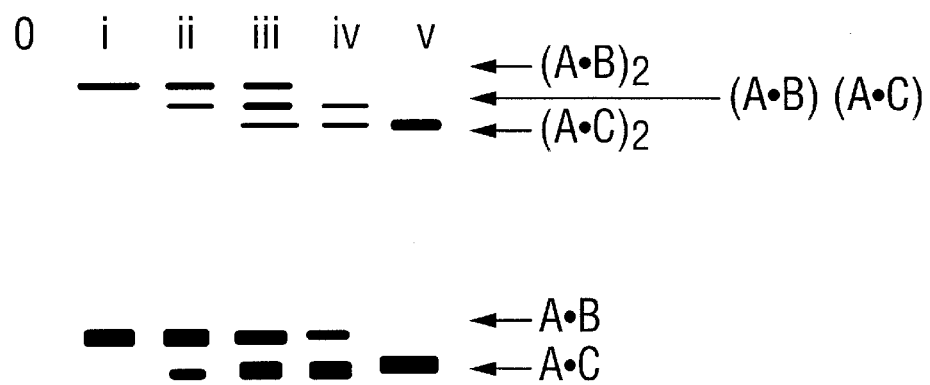
FIG. 15
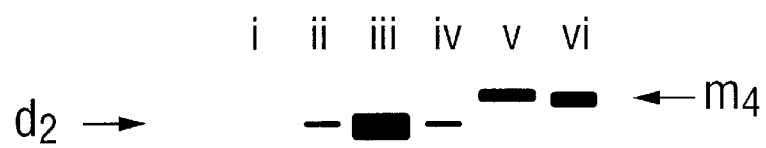
FIG. 16

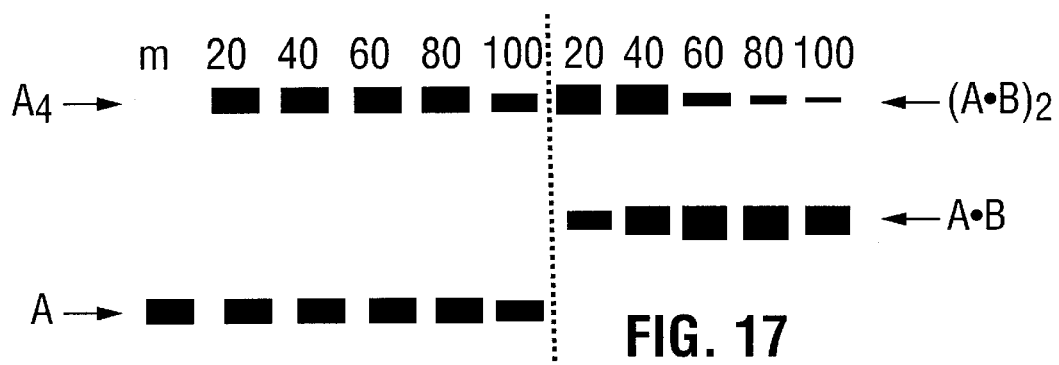
FIG. 17
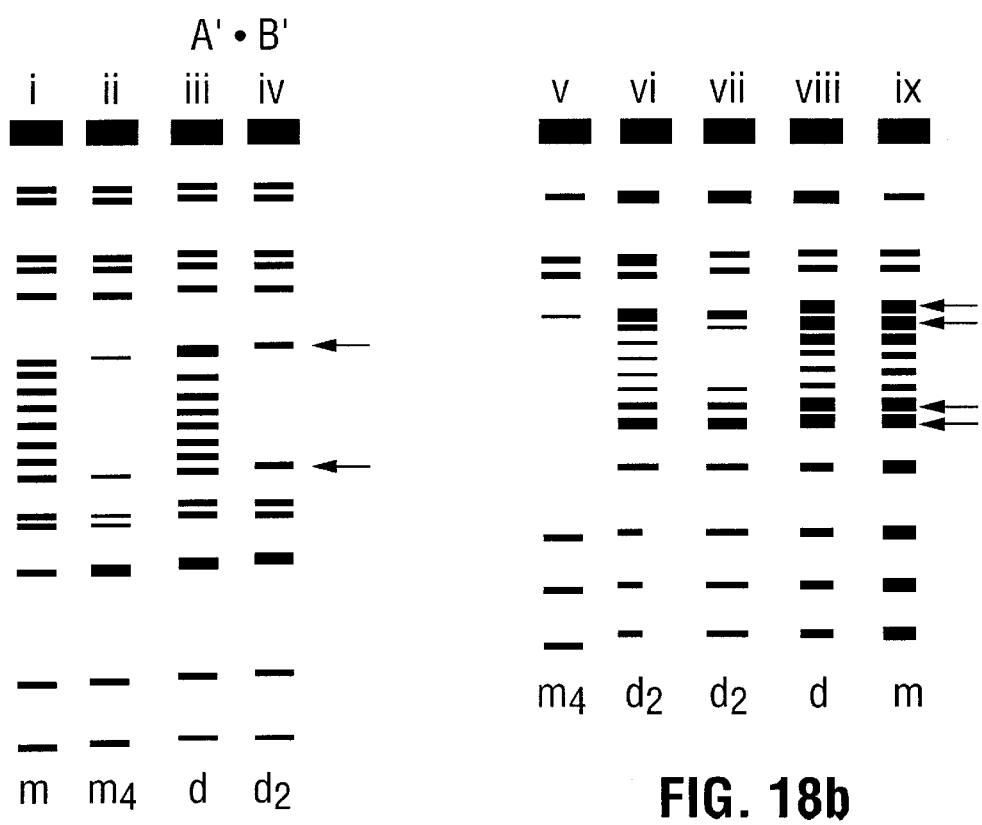
FIG. 18a
FIG. 18b

METHOD OF BINDING TWO OR MORE DNA DOUBLE HELICES AND PRODUCTS FORMED

RELATED APPLICATION

The present application claims benefit of provisional application "Method Of Binding Two Or More DNA Double Helices And Product So Formed", Ser. No. 60/019,795, filed on Jun. 14, 1996.

FIELD OF THE INVENTION

The present invention relates to synapsable nucleic acids, methods of binding nucleic acids into synapses and the products so formed. The present invention, in particular relates to synapsable deoxyribonucleic acid (DNA), methods of binding nucleic acids into synapses and the products so formed.

BACKGROUND OF THE INVENTION

Nucleic Acids, i.e. DNA and RNA which are naturally occurring biopolymers, have been recognized for their ability to form different structures and conformations which might be exploited to create complex superstructures in two and three dimensions using these polymers (Amato, 1993—See list of references.). Such "nanostructures" could find use in different applications, particularly as scaffolds for the attachments of other important molecules, such as enzymes, for use in bioreactors.

The major approach towards making these nanostructures has made use of stable multi-way, three-way, four-way, or higher, DNA double-helical junctions (Chen and Seeman, 1991; Seeman, 1991; Seeman et al., 1994). The approach in this line of work is to generate stable four-way junctions, a DNA structure in which four double-helical elements are joined together to give a cross-shaped or a scissor-shaped structure with four double-helical "arms". To form these structures, four synthetic DNA single-stranded molecules are assembled together with the appropriately complementary sequences. The assembled four-way junction is designed also to have "sticky" ends—approximately six unpaired nucleotides at the terminus of each of its four double-helical elements, which are able to transiently bind other, complementary "sticky" ends from other four-way junctions or double-helices. These transient bindings, mediated by Watson-Crick base-pairing, are then rendered permanent and stable by ligation with enzymes such as T4 DNA ligase.

Using this general strategy, complex geometric objects, with the topology—if not the shape—of cubes and octahedra have been constructed out of double-helical DNA (Chen and Seeman, 1991; Seeman, 1991; Seeman et al., 1994). The strategy for these constructions, however, has multiple steps, involving repeated events of prior assembling of the component four-way junctions, with their collection of sticky ends. The interaction of sticky ends, involving Watson-Crick interactions between single-stranded complementary elements, are difficult to control due to their rapid occurrence in aqueous conditions in the presence of almost any kind of salt and the need to ligate the sticky ended interactions, which requires the use of expensive ligating enzymes and accessory chemicals such as adenosine triphosphate (ATP). The efficiency of the enzymatic ligation reaction is all-important for the overall success of the enterprise—a lack of complete ligation in a multiple-step assembly procedure can severely compromise the overall yield of the final, desired product.

Another class of DNA-based superstructures has attempted to utilize the formation of guanine-guanine quartets to hold together component single-stranded DNA molecules in extended quadruple helices (G4-DNA) (Sen and Gilbert, 1991). Only single-stranded DNA molecules, containing guanine-rich motifs, are capable of forming these structures, summarized under the general description of "G-wires" (Lu et al., 1992; Sen and Gilbert, 1992; Marsh and Henderson, 1994; Chen, 1995; Marsh et al., 1995). A very important disadvantage to the G-wires technology is that the formation of these wires is extremely difficult to control. Products are invariably polydisperse, containing a variety of sizes and molecular weight classes. The precise nature of bonding is also difficult to control, as is the difficulty of creating branched structures. With the current state of know-how, it would be very difficult if not impossible to create precise geometric shapes, such as cubes, or even extended networked arrays of DNA sequences using the G-wire technology It is one of the objects of the present invention to obviate or litigate the above disadvantages with a new method for synapsing nucleic acids to create a nucleic acid superstructure. The term 'synapsis' is used to denote the ability of one nucleic acid to bind another nucleic acid at specific, predetermined sites.

One of the applications for which a nucleic acid superstructure may be used is signal amplification. Many of the high-sensitivity detection systems that are widely used in bio-medicine nowadays are based on signal amplification technologies. Some commonly used techniques are radio-immunoassays (RIA), ELISA methods, as well as Western Blots. These techniques detect very low levels of a specific protein, nucleic acid, or other antigens in biological samples such as bodily fluids like blood, semen, and saliva, or in environmentally important samples such as water from rivers and other bodies of water. These techniques also provide the foundation for diagnostic assays used widely to monitor diseases such as AIDS. Most signal amplification technologies use antibodies, in which specific protein (antibody) molecules are used both to recognize and bind specifically to the antigen molecule in question and then to amplify the 'signal' of the initial recognition event between antibody and antigen by many orders of magnitude. Without this amplfication step, the initial recognition event would be of low sensitivity, and therefore of little practical use. Thus, it is the amplification procedures which determine the sensitivity and, to a degree, the specificity of the diagnosis from the RIA, ELISA, and Western Blot techniques.

Fundamentally, in the techniques mentioned above, the initial recognition and binding of typically an antibody to an antigen molecule is followed by the binding of another set of antibodies to the first antibody. Thus, a monoclonal mouse anti-HIV antibody molecule might bind to an immobilized HIV antigen molecule in an ELISA plate. This is followed by the binding of secondary antibodies, eg. goat anti-mouse antibodies to the first, mouse antibody. Tertiary antibodies, eg. sheep anti-goat antibodies, are then bound to the secondary goat antibodies, and so on. At each stage of such secondary, tertiary, and further antibody additions, there is an amplification of the 'signal'; in other words, two goat antibody molecules bind to each mouse antibody, and two sheep antibodies bind to each goat antibody, and so on. In this way, a 'cascade' of antibody binding is produced. The end result is that numerous final antibodies may be immobilized to a single antigen molecule. The final antibodies may have a reporter molecule that may be used to produce a detectable signal of some sort eg. radioactivity, fluorescent labelling, or the activity of a coupled enzyme such as alkaline phosphatase.

It is, thus, another object of the invention to provide a novel and alternative means to antibodies as a basis for a signal amplification system by using synapsable DNA superstructures.

A number of investigators [Murphy et al., 1993; Arkin et al., 1996] have demonstrated the fast and relatively easy passage of electrons through a double helix. The delocalized pi-electrons of the stacked base-pairs at the heart of the double-helix are presumably the path of electron transfer. Murphy et al. have studied this system by intercalating an electron-donating inorganic metal complex between base pairs at one end of a short double helix, and by positioning an electron-accepting metal complex at the other end of the double-helix.

Overall, these experiments have raised the interesting possibility of using DNA as a wire in nano-technological applications. It is conceivable that simple electronic devices, such as inductors, capacitors, diodes, and transistors, might be designed from DNA. The size range of DNA-in the nanometer to micrometer size domain, its electron-conducting ability, its precise structural dimensions, and its ease of automated synthesis make it eminently suitable for the above goal.

However, there are some special problems associated with the use of DNA as a material for designing circuits. An important issue, and one that has not been discussed in the literature, is the problem of making conducting junctions with double-helical DNA. A three-way double-helical junction is shown in FIG. 1a and FIG. 1b and a four-way double-helical junction is shown in FIG. 2a. The conduction of electricity through double-helical structures in general is contingent on a continuous stacking of base-pairs. However, the folded forms of three-way and four-way junctions are such that one or more helical elements are invariably not stacked on the others, out of purely geometric constraints. The three-way junction, for instance, can exist in either as a 'Y' structure, shown in FIG. 1a, or as a 'T' structure, shown in FIG. 1b, (Duckett & Lilley, 1990). Which structure is adopted is dependent on the identity of the base-pairs at the junctions. It can be seen that in either conformation, these conventional three-way junctions do not allow passage of electrons from an input arm to all of the other arms.

In a standard four-way junction made up of four double-helical elements, as shown in FIG. 2a, the double-helices arrange themselves into two sets each of two stacking double-helices; however, between each set there is no stacking of base pairs. Consequently an electron entering through any one of the double helices would be propagated rapidly through only its stacking partner, and not to the other two double-helical elements. Thus, a standard four-way junction also does not allow passage of electrons from an input arm to all of the other arms.

It is, therefore, another object of the invention to provide a better means for constructing conducting junctions using synapsable DNA superstructures.

It is yet another object of the invention to provide other applications of synapsable DNA superstructures.

SUMMARY OF THE INVENTION

The present invention, in one aspect, provides a nucleic acid complex having a double-stranded section with a domain of guanine nucleotides. The guanine nucleotides form a pair of substantially contiguous guanine sequences that interact together to form stable bonds. In other words, the guanines in one guanine sequence of one section interact with guanines in the other guanine sequence of the other section to form "mismatched" base-pairs in a guanine domain. The "mismatched" base-pairs in the guanine domain have the property of additionally binding or 'synapsing' to "mismatched" base-pairs in another guanine domain to form stable guanine quartets. The nucleic acid complex may be comprised of single-stranded or double-stranded deoxyribonucleic acid (DNA) or ribonucleic acid (RNA). The double-stranded DNA complex with a synapsable domain may have particular coding sequences or may not have any coding sequence. Furthermore, the guanine sequences in the domain may be in a parallel orientation to each other or in an antiparallel orientation to each other. Most importantly, the guanine domains may be tagged either chemically or contain non-guanine RNA or DNA bases to give specificity to the domain.

In another aspect of the invention, a method of forming nucleic acid superstructures is described. Nucleic acid single strands with guanine sequences are synthesized and the strands allowed to "self-associate" to form a double helix. Guanines from one guanine sequence interact with guanines from a second guanine sequence to form stable hydrogen bonds and a guanine domain within the double helix. The guanine domains endow individual nucleic acid helices which normally repel each other and do not have any simple means for binding one another the unique property of synapsis, or the ability to bind one another at specific, predetermined sites. Simple mixing of two appropriate doctored nucleic acid complexes therefore leads to this form of synapsis, often even at room temperature, and in buffered aqueous solutions.

In another aspect of the invention, there is provided the nucleic acid superstructure formed in accordance with the method described above and which comprises two or more nucleic acid molecules modified to have synapsable guanine domains. The nucleic acid superstructure may form with the interaction of chemically tagged guanine domains in nucleic acid complex with identical chemically tagged guanine domains in another nucleic acid complex.

In another aspect of the invention, there is provided major applications relate to the emerging technology of nucleic acid nanostructures with particular emphasis on the ability to easily create a signal amplification system dependent on nucleic acids instead of antibodies. Other applications provided relate to scaffolds, wires, and other electronically- and medically-relevant structures out of this robust material.

In signal amplification systems, DNA provides a number of unique advantages over antibodies. First, synapsable DNA superstructures, being DNA, are highly negatively charged, and are therefore repulsive towards one another unless present under the specific conditions conducive to synapsis. Second, in addition to this general repulsive property, synapsable DNA superstructures are composed entirely of double-helical DNA, which cannot base-pair with other DNA molecules. These properties of being fully double-stranded, yet capable of synapsis under defined conditions, and being highly negatively charged and therefore repulsive to DNA and RNA molecules in general, should allow for a very high specificity of signal amplification, with a high signal-to-noise ratio. Third, the synapsable DNA superstructures have considerably lower molecular weights, typically 50,000 to 70,000 Daltons, than antibodies, and could therefore be more easily taken up by living cells than antibodies. Fourth, the amplification factor for each synapsable DNA superstructure in a signal amplification scheme could be four to five-fold per round compared typically with an amplification factor of two per round per antibody molecule. Fifth, DNA is intrinsically a material of high chemical inertness and stability. Sixth, DNA, as synthesized on automated DNA synthesizers, is a relatively cheap material, and could be produced in bulk. Automated synthesis, furthermore, permits both easy and precise attachment of such entities as fluorescent labels, or amino or carboxyl residues for the post-synthetic attachment of enzymes to synapsable DNA superstructures. Comparable derivatizations of proteins, including antibodies are, by contrast, both more haphazard and less precise.

A signal amplification system comprising propeller shaped molecules with two or more arms and each arm having a synapsable guanine domain is provided. The propeller shaped molecules may be customized by the attachment of a probe to serve as "primary antibodies" as well as "secondary antibodies".

The present invention facilitates the construction of junctions in DNA wires. The synapsable guanine domains allow the stacking of base pairs in a junction of two double-stranded helical DNA so that electrons can flow from one double-stranded helical molecule to another.

The present invention further provides for a network of nucleic acids associated through the synapsable guanine domains. This network may serve as a scaffold for enzyme complexes, used to create quasi-crystalline structures, or to generate electronic circuits.

The present invention further provides for a method of chromatography using synapsable DNA complexes to purify DNA moleules out of a mixture.

In summary, this invention where two or more nucleic acid helices are stably associated is novel and unexpected. By engineering into nucleic acids specific sequences, a nucleic acid complex, with the property of binding to other similar complexes, is generated. The association of such complexes results in the formation of nucleic acid superstructures that may be employed in nucleic acid nanaostructure technology.

BRIEF DESCRIPTION OF THE DRAWINGS

The novel features believed to characterize the invention are set forth in the appended claims. The invention, itself, however, as well as other features and advantages thereof, will be best understood by reference to the detailed description which follows, read in conjunction with the accompanying drawings, wherein:

FIG. 5a represents a double-stranded helical DNA with a guanine domain;

FIG. 5b represents double-stranded helical DNA with a guanine domain and a thymine buffer at each end of the guanine domain;

FIG. 5c is a truncated version of FIG. 5a;

FIG. 10a is the nucleotide sequence of a propeller shaped molecule with three DNA strands, each strand having two guanine sequences that interact with each other to form three guanine domains;

FIG. 10b represents a propeller shaped molecule with the termini closed with covalent bonds;

FIG. 10c represents a propeller shaped molecule with the termini closed with polyether bridges;

FIG. 11a represents a propeller shaped molecule with an identical guanine domain on each arm;

FIG. 11b represents a propeller shaped molecule with a different guanine domain on each arm;

FIG. 11c represents the interaction of a guanine domain on an arm of a propeller shaped molecule with an identical guanine domain on an arm of a second propeller shaped molecule;

FIG. 12 represents the signal amplification cascade using the propeller shaped molecules;

FIG. 13 represents a three way junction constructed with synapsable DNA;

FIG. 14 is a polyacrylamide electrophoresis gel showing the results of a timecourse for incubating sample A.B for various amounts of time;

FIG. 15 is a polyacrylamide electrophoresis gel comparing the mobilities of samples A.B and A.C and the guanine quartets formed;

FIG. 16 is a polyacrylamide electrophoresis gel showing the results of the incubation of A.B in 1 M $Li^+$, $Na^+$, and $K^+$, respectively in the absence of magnesium;

FIG. 17 is a polyacrylamide electrophoresis gel showing the melting profiles of $(A.B)_2$ and of the parallel quadruplex $A_4$ at low concentrations of DNA in a low salt buffer;

FIG. 18a is polyacrylamide electrophoresis gel showing methylation protection patterns of complexes formed by A' and B'; and, FIG. 18b is polyacrylamide electrophoresis gel showing methylation protection patterns of complexes formed by A and B.

DETAILED DESCRIPTION WITH REFERENCE TO THE FIGURES

The preferred embodiment of the invention has been very generally described in a scientific paper that has appeared in the *Journal of Molecular Biology* (Venczel and Sen, 1996) (incorporated herein by reference).

In a preferred embodiment of the invention, double-stranded helical DNA is used. Double-stranded helical DNA, as opposed to single-stranded DNA, has the notable properties of chemical stability; and structural rigidity in aqueous solutions. It is also a polymer which provides regularly spaced sites at the phosphate, sugar, and base moieties of each nucleotide unit for precisely predetermined attachment of one or multiple extraneous chemical groups. Such unmodified DNA strands are easily and inexpensively synthesized in automated DNA synthesizers. Double-stranded helical DNA, with its compactly stacked central core of base-pairs has the further ability to conduct electricity, i.e. to allow the rapid passage of electrons down its length owing to the mobility of the $\pi$-electrons of the stacked base-pairs running down the core of the double-helix (Murphy et al., 1994). Furthermore, double-stranded helical DNA in contrast with single-stranded DNA has the advantageous property that in aqueous solution distinct double-helices tend not to bind or interact favourably with one another except under extraordinary solution conditions, such as in the presence of cations containing three or more positive charges. The high negative charge-density along the backbone of the double-helix, as well as the absence of possibilities for further base-pairing, create a net repulsive interaction between any two double helices.

Figure 3:
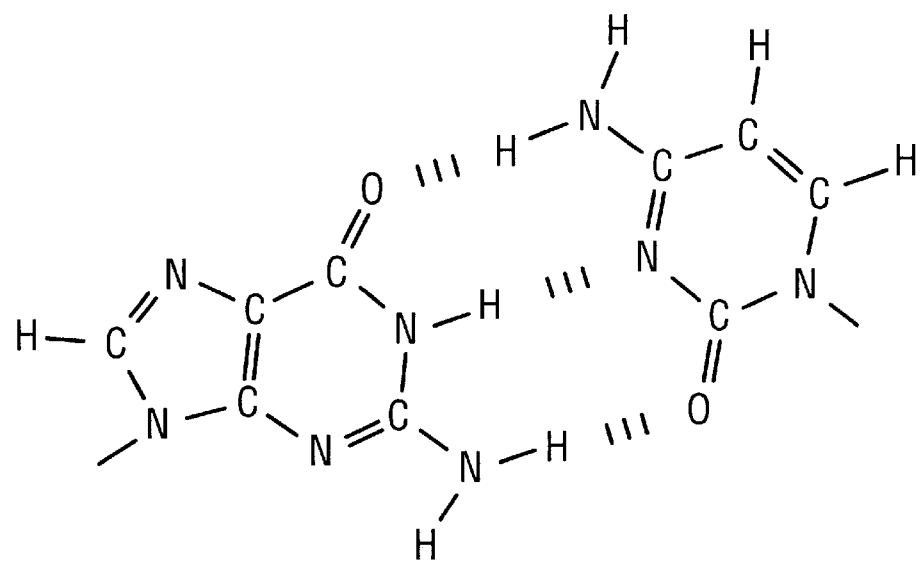
FIG. 3 represents a Watson-Crick model of guanine to cytosine bonding.
Figure 4:
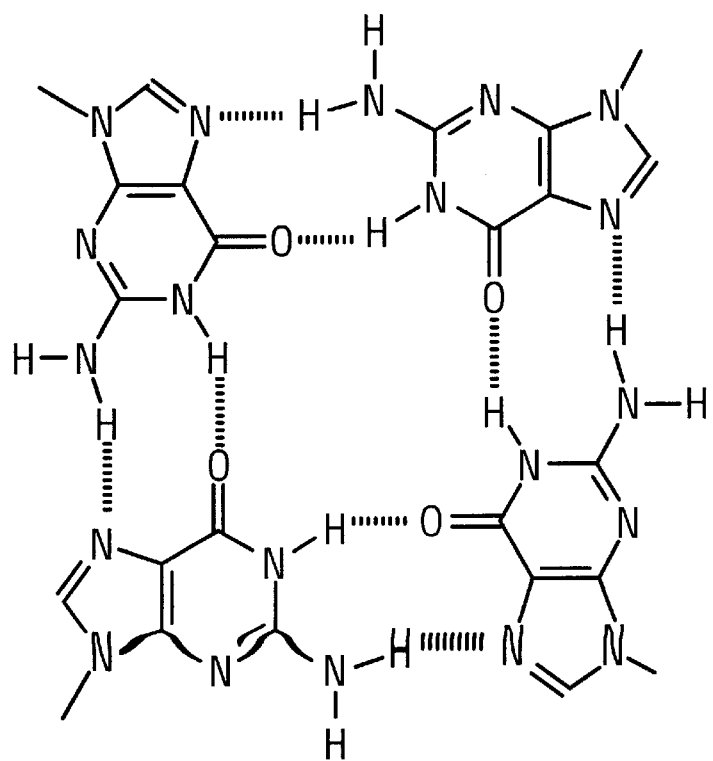
FIG. 4 represents a proposed model of guanine to guanine bonding.

The starting DNA strand, from which the synaptic double-helices are assembled, is synthesized in automated DNA synthesizers, which themselves are now cheap and widely available. The standard synaptic DNA complexes may contain only the standard DNA nucleotides, and no extraneous, non-DNA related chemical modifications. The synaptic property arises out of a mismatch pairing of guanine to guanine, instead of the guanine 1 to cytosine 2 Watson-Crick base pairing found in normal DNA (FIG. 3). A proposed model of guanine to guanine mismatch pairing is shown in FIG. 4 (Chen, 1995). However, since automated DNA synthesizers also allow the automated attachment of a host of unusual chemical groups to any point or points along the length of either strand of DNA used to form a double-helix, at precisely 3.4 Angstrom intervals, chemical groups may be inserted onto the DNA strand. Thus, two double-helices made to synapse, could bring into proximity two or more distinct chemical groups which were attached, say, to the two constituent double helices of a synapsed superstructure, perhaps for enzymatic purposes, such as creating a "catalytic triad" found in protein-digesting enzymes such as trypsin.

It is not necessary that the starting DNA single strands have any particular or unique coding configuration. In fact, the DNA need not contain coding sequences at all. However, useful double-helical DNA sequences can be incorporated into the starting and final structures. What is essential is that, within the complex of each two single strands of DNA so formed, there be at least one contiguous guanine-guanine mismatch region. Examples of complexes with guanine-guanine mismatch regions are shown in FIGS. 5a, 5b, 5c. Although the guanine domains in FIGS. 5a, 5b, 5c have eight guanines in the guanine sequence, the number of guanines can be varied from one to infinity. The optimal number of guanines in the guanine sequence can range from two to eight. It should be noted that engineering guanine-guanine mismatch base-pairs into Watson-Crick helices result in a relatively small change in the overall physical properties of the modified complexes. It should be further noted that guanines present as guanine-cytosine base pairs within Watson-Crick double-helices are unable to form guanine quartets.

Figure 6A:
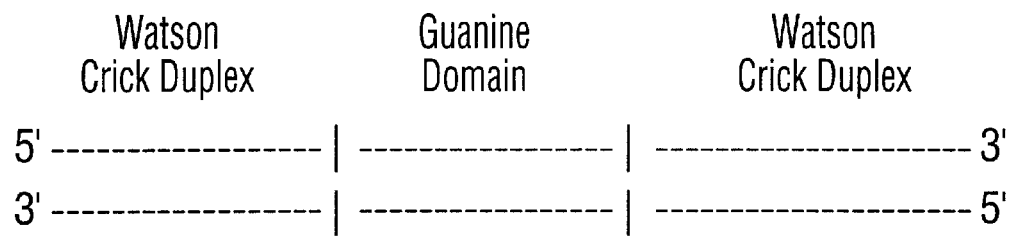
FIG. 6a represents a double-stranded helical DNA with a guanine domain where the two guanine sequences are in antiparallel orientation.
Figure 6B:
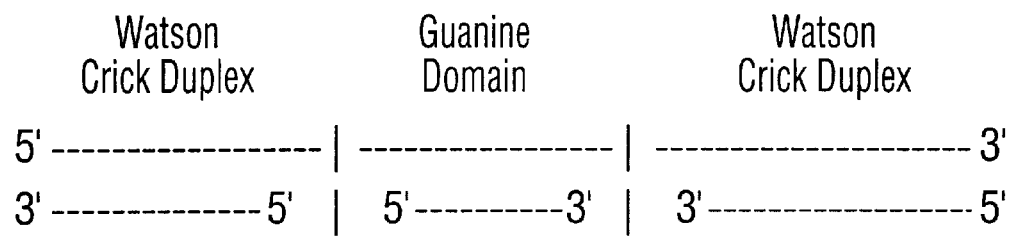
FIG. 6b represents a double-stranded helical DNA with a guanine domain where the two guanine sequences are in parallel orientation.

The polarity of the guanine sequences in the complex may have the oppposite orientation as in regular antiparallel complex DNA where the two strands have opposite polarity, one with a 5'→3' and the other complementary strand a 3'→5' orientation. FIG. 6a shows a double-stranded helical DNA with a guanine domain where the two guanine sequences are in antiparallel orientation. Guanines or synapsis sequence on one strand of the double-stranded helical DNA may also be synthetically made with a polarity reverse to the polarity of the overall strand polarity. FIG. 6b shows a double-stranded helical DNA with a guanine domain where the two guanine sequences are in parallel orientation.

The parallel synaptic element is able to form parallel stranded guanine quartet structures as opposed to the antiparallel guanine quartet structures formed by the regular antiparallel guanine-guanine mismatch containing DNA complexes. Synapsis between parallel elements results in a more stable quartet structure.

Methylated cytosines may be incorporated into the synaptic element at predetermined positions to allow modulation of the synapsis event between two complexes. The methylated cytosines participate in the guanine quartet via stacking interactions and not through Watson-Crick guanine-methylated cytosine (G-$^m$C) base-pairing interactions. Other modified bases or "tags" may be incorporated in the guanine sequences.

Unlike the formation of Watson-Crick base pairs which are able to form under a wide variety of salt and buffer conditions, and therefore have the potential to complicate the sticky-end mediated base-pairing used in the four-way junction-based technologies, the formation of guanine-quartets in accordance with the present invention is easier to control. In order to form the superstructures or nanostructures of the present invention, the complexes are incubated in near-physiological buffers where guanine-guanine mismatched base-pairs within double-stranded helical DNA seek each other out and bond together to form stable guanine-quartets. The types of buffers used for the formation are widely known in the art and include Tris, Hepes, Taurine, to name a few. Inclusive in these buffer solutions are cations that are either able to impede or facilitate formation of and or stabilize guanine quartet structures. The cations most notable for these varying abilities are the alkali cations— $Li^+$, $Na^+$, $K^+$, $Cs^+$, $Rb^+$; the earth alkaline cations—$Mg^{2+}$, $Ca^{2+}$, $Ba^{2+}$, $Sr^+$; and the rare earth element cations. Varying the buffer components provides a simple means to modulating formation of desired guanine quartet structure or structures. Magnesium ions aid the formation of synaptic structures. In the absence of magnesium ions, guanine-quartet based-structures require potassium ions for their formation and stabilization. In the presence of the otherwise similar lithium ion, the guanine-quartet based structures do not form. Thus, depending on the balance of lithium and potassium in a solution, it is possible to fine tune the rate and extent of synapsis of the guanine-rich synaptic elements. For example the simplest buffer to promote formation of the synapsed complex or superstructure from complexes is 50 mM Tris, 1M NaCl, 1 mM EDTA. A better buffer of 10 mM Tris pH 7.5, 200 mM KCl, 50 mM LiCl, 1.5 mM $MgCl_2$ provides optimal concentrations of lithium and magnesium ions.

Figure 7:
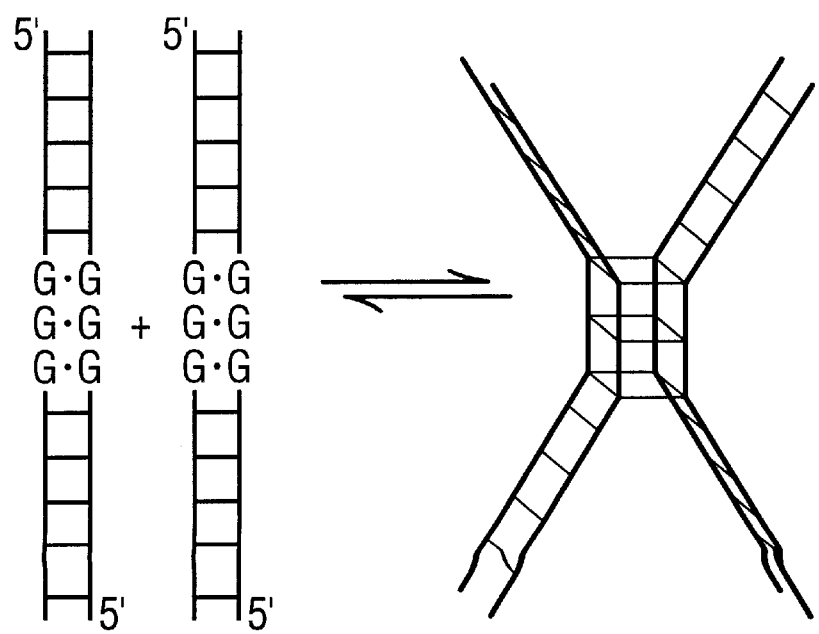
FIG. 7 represents the formation of a quadruplex resulting from the interaction of two guanine domains.

Once incubation has taken place and the synapsed guanine domains have formed the guanine quartet structures as shown in FIG. 7, the structures are purified from the reaction mixture either by PAGE, HPLC, size exclusion chromatography, ion chromatography, ligand binding chromatography. The method of purification is wholly dependent on the further purpose of the synapsed structure. The purified guanine quartet structures, once they are separated from their reaction mixtures, can be further concentrated to provide a stable stock solution for future application.

Guanine quartet containing structures, as a class, have high thermal stability and G-mediated synapsed structures are no exception to this. Therefore, it is possible to design synaptic motifs within double-helices that are able to remain synapsed stably, without the necessity for some sort of chemical and/or enzymatic ligation to hold them together.

Figure 8:
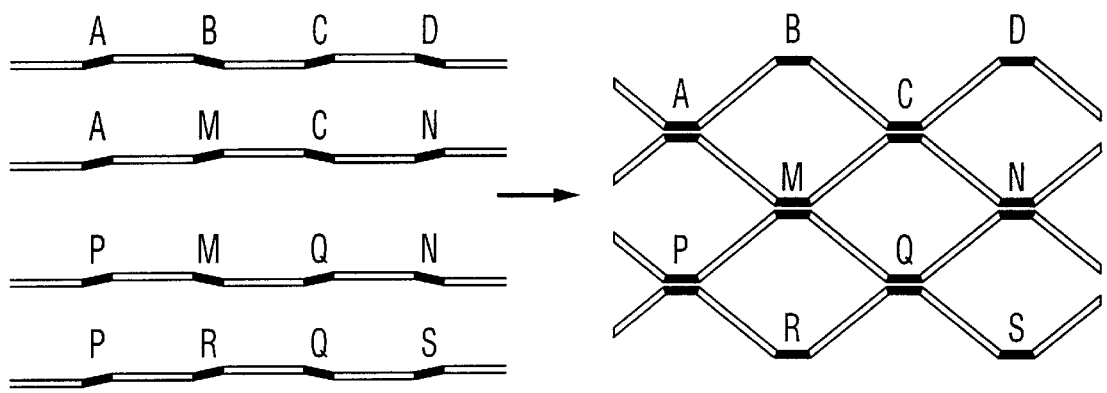
FIG. 8 represents the formation of a DNA network from double-stranded helical DNA with multiple guanine domains, each domain having a chemical tag such that domains with identical tags form bonds.

Synaptic guanine domains can carry a variety of guanine-rich mismatches incorporating other, non-guanine bases as tags. These natural or artificial DNA or RNA bases may be arranged in any order within the guanine domain. Synaptic guanine domains may carry also chemical tags comprising of chemical functionalities that are unrelated to any natural component of DNA or RNA. These tags can be arranged so that "like" synapses to "like". In other words, if a given double helix is made to contain two distinct synaptic tags, A and B, with dissimilar sequences, it is possible for tag A to synapse exclusively to the tag A of another complex, and likewise for the tags B. The larger implication of this is that it is possible to create elaborate "network"-like structures by mixing appropriate doctored double-helices, as shown in FIG. 8.

Figure 9:
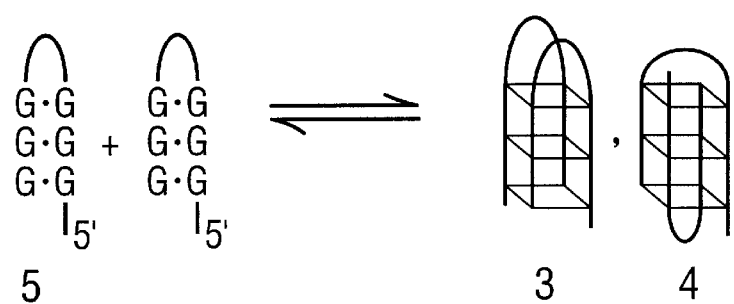
FIG. 9 represents the formation of the guanine domain in single-stranded DNA and the formation of the quadruplex from these guanine domains.

In other embodiments, single stranded DNA with blocks of contiguous guanines sequences may also be used. For example, single stranded DNA can form a hairpin loop where the DNA strand 'loops' back on itself if complementary bases are present in two different areas of the DNA strand. As shown in FIG. 9, single-stranded DNA with more than one guanine sequence of contiguous guanines may loop back so that the guanine sequences are in proximity allowing guanines from one sequence to interact with guanines from a second sequence to form stable bonds and a guanine domain, 5. Guanine domains from one hairpin loop thus formed may synapse with guanine domains from another similar hairpin loop resulting in guanine quadruplexes 3 and 4, as shown in FIG. 9.

It should be noted that there are some viral RNAs that are double stranded. So a synapsis of two guanine-guanine domains from two such double-stranded RNA is possible. In addition, single-stranded RNA may form quartet structures in a similar manner to single-stranded DNA. Although only one polynucleotide chain is usually present, RNA does posess regions of double-helical coiling similar to single-stranded DNA where the single chain loops back upon itself if complementary bases are present. Thus RNA with two or more guanine sequences may form guanine domains and the guanine domains may synapse to form guanine quartets.

Furthermore, a nucleic acid complex comprising one nucleic acid strand of ribonucleic acid with a guanine sequence and a second nucleic acid strand of deoxyribonucleic acid with a guanine sequence may be constructed. These complexes would synapse with other complexes with guanine domains. In addition, chimeric RNA as well as chimeric DNA strands may be used to form a synapsable complex.

The uses of the guanine-mediated "superstructure" or synapsis of the present invention include, but are not limited to, the following:

(1) Signal Amplification

Specialized DNA structures containing 'synapsable domains' might be constructed for signal amplification. A preferred embodiment, as shown in FIG. 10a, comprises of three DNA strands with two parts. A first strand contains two guanine sequences and DNA sequences that are complementary to a second DNA strand and to a third DNA strand. Thus one guanine sequence from a first DNA strand forms a guanine domain with a guanine sequence from a second DNA strand and the other guanine sequence forms a guanine domain with a guanine sequence from the third DNA strand. The complementary DNA forms double-stranded helical structures with the complementary DNA on the second and third strand. In the same way, the second DNA strand interacts with the first and third DNA strands and the third DNA strand interacts with the first and second DNA strands resulting in a propeller shaped structure with three guanine domains. The three-armed propeller-shaped DNA molecules shown in FIGS. 10a, 10b, 10c contain three double-helical arms connected together in a three-way junction. Such DNA structures might bind multiple structures through their guanine domains under appropriate solution conditions (Venczel and Sen, 1996).

Each of the propeller arms may be designed containing identical synapsable motifs in each arm or three different motifs according to the specificity of synapsis, and the nature of the amplification cascade required. For example, motif A is present in each arm in FIG. 11a while in FIG. 11b, three different motifs, A, B, C are present. Referring to FIG. 11c, any of the arms with motif A of a propeller shaped molecule in FIG. 11a will synapse with only motif A of a propeller shaped molecule in FIG. 11b.

The propeller-shaped molecules could be stabilized by covalently closing the three termini of the DNA as shown in FIG. 10b or connecting the three termini with non-standard, polyether bridges as shown in FIG. 10c. Other chemical means may be employed to close the termini of the DNA. This closure would ensure a high physical robustness in terms of high thermal stability as well as chemical stability such as protection from possible exonuclease enzymes present in biological samples being assayed.

The way that these propeller-shaped synapsable DNA molecules ("PSSDs") would be used is shown in FIG. 12. An initial recognition event of an antigen, indicated, in this example, as a DNA or RNA "substrate" 6 in the figure, by an antibody molecule, indicated as "DNA or RNA probe" 7 in the figure, could undergo a rapid and specific signal amplification by the use of PSSDs. As shown in the figure, such PSSD units would specifically and signficantly bind to one another via the guanine domains 9 to form guanine quadruplexes, as shown, in a cascade fashion, in the presence of potassium ions. The presence of a "reporter" radio-, fluorescent-, or enzyme-labels, shown as black filled circles 8, on two arms of each PSSD molecule, would give rise to an enormous signal for each molecule of antigen present.

In other embodiments, PSSDs with a larger number of arms than three may be constructed. A PSSD molecule containing four, five or more arms can be constructed. The probe could be substituted with any antibody like molecule while the substrate could be any antigen like molecule.

(2) Multiple-way Conducting Junctions in DNA Wires

Figure 1A:
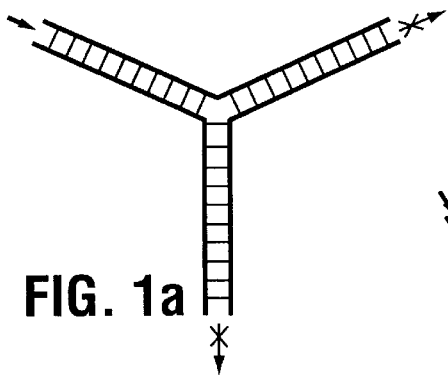
FIG. 1a represents a three-way double helical junction in the shape of a "Y" with the direction of the electron flow.
Figure 1B:
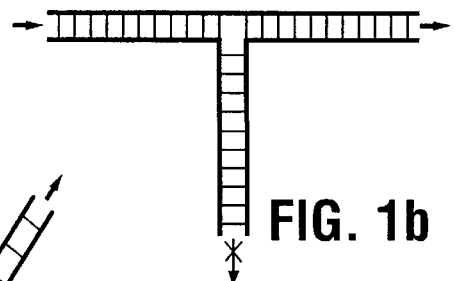
FIG. 1b represents a three-way double helical junction in the shape of a "T" with the direction of the electron flow.
Figure 1C:
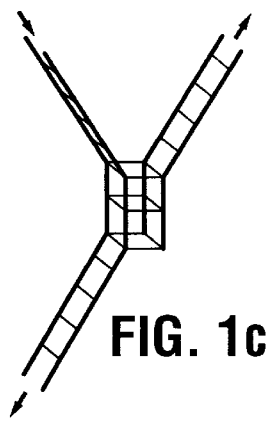
FIG. 1c represents a three-way double helical junction constructed from synapsable DNA, comprising of double-stranded helical areas and guanine domains, with the direction of the electron flow.

Referring to FIG. 13, a preferred embodiment of a "three-way junction" may be created from guanine synapsable double helices such that electron flow from any of the three helical arms to the other two occurs freely. The synapsed region in the double helices contains not base pairs but guanine-quartets, which would be expected to stack upon base pairs on either side, and therefore provide a base-stacked continuum between the base-pairs of all three double-helical arms. A model of a three way junction is shown in FIG. 1c.

Figure 2A:
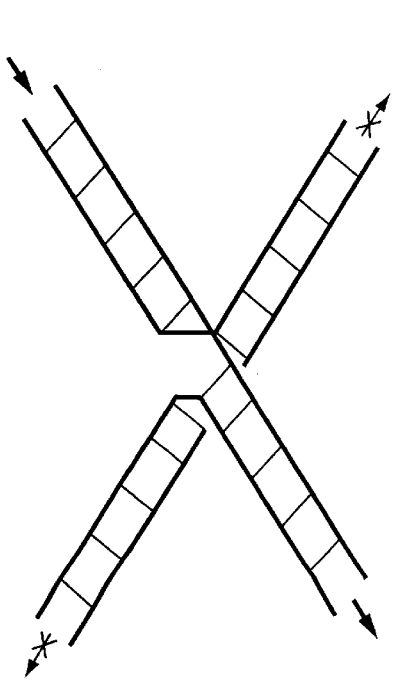
FIG. 2a represents a four-way double helical junction with the direction of the electron flow.
Figure 2B:
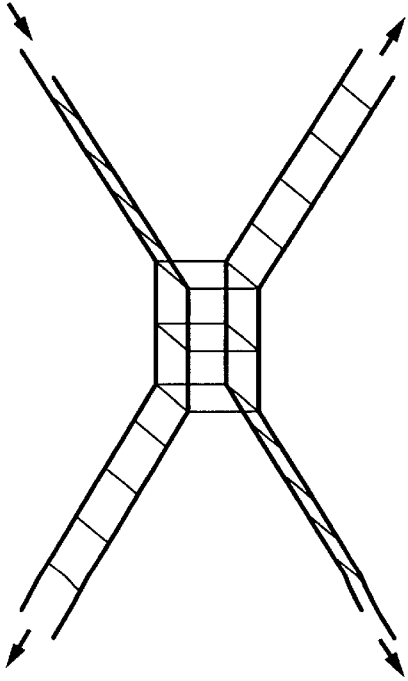
FIG. 2b represents a four-way double helical junction constructed from synapsable DNA, comprising of double-stranded helical areas and guanine domains, with the direction of the electron flow.

Referring to FIG. 2b, a "four-way junction" may be created from G-synapsable double helices such that electron flow from any of the four helical arms to the other three occurs freely. With the G-synapsed complexes, all four double-helical elements should have base-stacks shared between them; one would then expect electrical conduction to take place between all four helices.

(3) Scaffolds for Structural Studies and for the Attachment of Heterologous Functionalities Precisely calibrated two- and three-dimensional nanostructures could be created using the right combinations of synapsable double helices. Particularly important DNA sequences, such as those involved in gene expression and in protein binding, could be repeated in regular arrays to create quasi-crystalline structures, which would facilitate the investigation of their structures with X-Ray diffraction. Growing a conventional crystal from the DNA, especially if it is associated with a protein is generally difficult.

Precise two- or three-dimensional scaffolds made with synapsable DNA could provide a resilient and stable network for the assembly of artificial enzymes. Thus, for example, glucosides enzymes, such as xylanase, of great interest in the industrial digestion of wood and wood products to simper sugars, contains precisely separated carboxylate groups in their active sites. Such enzymatic activities could be assembled on a repeating DNA scaffold for mass-utilization.

(4) Potential Support for Biological Tissues Suitable for Transplantation, Such as Artificial Skin A number of prominent biomedical technologies have come to the forefront in recent years, such as the development of artificial skin, which can be used to help burn victims. Any kind of biological tissue with a large surface area would require a network of connective tissue beneath, made up of proteins, or indeed, "crosslinked" DNA, such as produced by G-mediated synapsis.

(5) Chromatographic Systems

G-mediated synapsis, as described herein, works best in the presence of the salts of potassium and almost not at all with the salts of the similar metal, lithium. A certain synapsable domain could be localized on a chromatographic column in the unsynapsed form, in the presence of lithium. Other synapsable DNA complexes which were part of a complex mixture could then be added to the column. Upon the addition of potassium only the added synapsable DNA complexes, out of the complex mixture, would adhere to the column by synapsing with the domain already immobilized on the column. Everything else would wash away. The synapsis could then be dissolved, with a minimal of perturbation of salt or temperature, by incubation with lithium. This sort of technology could be of considerable use for isolating rare DNA-binding proteins from special types of cells, such as cancer cells.

(6) Wires in Electronic Circuits

A nucleic acid network formed by G-mediated synapsis could be laid down on an appropriate surface and the DNA selectively coated with gold by standard techniques to provide ultraminaturized electronic circuits.

EXAMPLES

Example 1

The goal was to test whether a group of contiguous G—G mismatches (a "guanine domain") within a Watson-Crick complex might confer a stickiness, or tendency to dimerization, to these sites within the complexes. Models for G—G mismatch base-pairing have incorporated several possible hydrogen-bonding schemes of which only a standard, asymmetric, Hoogsteen interaction would permit dimerization of G—G base-pairs to quartets (FIG.4).

To test whether a series of contiguous G—G mismatches within a complex would allow its dimerization via quartet formation, the complex A.B was assembled (FIG. 5a), which had eight mismatched G—G pairs within a Watson-Crick framework. To allow the guanine domain greater base-pairing and conformational flexibility, a second complex, A'.B', which incorporated T—T mismatches as buffers between the G-domain and the Watson-Crick domains, was assembled (FIG. 5b). The thermal stabilities of A.B and A'.B' and of their purely Watson-Crick counterparts, which substituted G=C and A=T base-pairs for G—G and T—T mismatches were determined from melting experiments carried out in a Cary 3E spectrophotometer. A.B and A'.B' in TELi buffer (10 mM Tris (pH 7.5), 1 mM EDTA, 50 mM LiCl), melted at 66° C. and 61° C., respectively; whereas, their Watson-Crick counterparts melted at 77° C. and 78° C., respectively.

Both A.B and A'.B', incubated separately in near-physiological buffers such as TKMg (10 mM Tris (pH 7.5), 200 mM KCl, 50 mM LiCl, 11.5 mM $MgCl_2$), gave greater molecular mass products that appeared as low mobility complexes in non-denaturing gels. Since the thymine "buffers" of A'.B' appeared not to provide any special advantage in this respect, most of the experiments were carried out on the complex A.B. FIG. 14 shows a time-course for incubating a gel-purified sample of A.B., at a 14 $\mu$M complex concentration, in TKMg buffer (10 mM Tris (pH 7.5), 200 mM Kcl, 50 mM LiCl, 11.5 mM $MgCl_2$), at 37° C. Incubations were for: (o) no incubation; (a) 15 minutes; (b) 30 minutes; (c) one hour; (d) 2 hours; (e) 4 hours. Complex A.B was gel-purified on a native 6% polyacrylamide gel, eluted into TELi buffer (10 mM Tris (pH 7.5), 1 mM EDTA, 50 mM LiCl), and used without further purification or concentration. Aliquots of eluted A.B (14 $\mu$M final complex concentration) were made to TKMg buffer (see above) at different times and incubated at 37° C. Incubated samples (containing equal amounts of DNA and of counts) were loaded onto a non-denaturing 8% polyacrylamide gel containing 50 mM Tris borate, 10 mM KCl, 2 mM MgCl. The gel was dried and autoradiographed following standard protocols.

By one hour, more than 50% of the complex had converted to a new, lower mobility, complex. The rate law for this transformation appeared complex, conforming to neither the first nor the second-order formalisms.

To demonstrate that the new, low-mobility complex corresponded to a dimer of the complex A.B, a mixing experiment was carried out, in which gel-purified complexes A.B and A.C (FIG. 5c) (A.C was a truncated version of A.B, with a slightly faster mobility) were incubated with high salt, either individually, or in mixtures of varying molar ratios. Complexes A.B and A.C were incubated individually or in mixtures of varying molar ratios.

FIG. 15 shows the result of the incubations. Lane O, oligomer A; lane I, A.B alone; lanes ii to iv, A.B:A.C=3:1, 1:1, 1:3; lane v, A.C alone. Samples of end-labeled A.B and A.C complexes were gel-purified and eluted (as above) and used without precipitation in ethanol. Samples (30 $\mu$l, each containing a total DNA concentration of 1.6 $\mu$M) were made to TELi+1 M NaCl and incubated overnight at 37° C. Samples were analyzed on an 8% polyacrylamide gel run in 50 mM TBE buffer+10 M KCl. The extreme left lane shows a 10 bp ladder. The complex A.B (48 bp) runs as expected between the 40 and 50 bp standards. However, $(A.B)_2$ runs with ~120 bp, suggesting both a complex geometry for that species and that it is not an end-to-end dimer of the complex A.B. FIG. 15 shows that three product bands arose from the mixtures, corresponding to $(A.B)_2$, $(A.B).(A.C)$, and $(A.C)_2$, indicating that the salt-induced product was unequivocally a dimer of the complex.

Example 2

An earlier study on a G-DNA complex had reported poor kinetics of its formation in the presence of potassium relative to sodium, however, the thermodynamic stability of the potassium form was significantly greater. It appears to be a general property of G-DNA complexes (including these synapsed complexes, data not shown) that the potassium complexes have significantly higher thermodynamic stability than their sodium counterparts. The large kinetic difference sometimes seen between the formation rates in the presence of potassium versus sodium can be diagnostic for the presence of G-quartets, and usually can be overridden by the inclusion of magnesium in incubations. The incubations of A.B in magnesium-containing buffers, which contained also either sodium or potassium, did not show appreciably different kinetics. However, FIG. 16 shows the result of incubating A.B in the presence of different alkali cations such as 1 M $Li^+$, $Na^+$, and $K^+$, respectively, in the absence, of magnesium. The kinetics followed the order: $Na^+>>K^+>Li^+$ (lanes iii, iv, ii). Gel-purified complex A.B in TELi buffer, as above, was divided into 5 $\mu l$ samples containing 2.0 $\mu l$ of DNA each, made to 1 M LiCl and Kcl, respectively, and incubated at 37° C. for one hour. Samples of the single strands A and B (which, in storage had formed small quantities of their respective parallel quadruplex complexes, $A_4$ and $B_4$), were run for comparison. Samples were analyzed in a non-denaturing 6% gel containing 50 mM TBE+ 10 mM KCl. The gel shows the results of the following incubations of A.B: lane I, TE+50 mM LiCl (buffer TELi); lane ii, TELi+1 M LiCl; lane iii, TELi+1 M NaCl; lane iv, TELi+1 M Kcl. Lanes v and vi show single-stranded oligomers A (lane v) and B (lane vi), with their respective parallel quadruplex complexes, $A^4$, and $B^4$. Labels: m, oligomer A (lane v), B (lane vi); $m^4$, $A^4$ (lane v) $B^4$ (lane vi); d, complex A.B; $d^2$, synapsed complex (complex dimer).

The synapsed-complex complex $(A.B)_2$ (labelled $d_2$ in these lanes) had a slightly faster, though reproducible, mobility than those of the corresponding parallel quadruplexes, $A_4$ and $B_4$ (labelled $m_4$, and formed, separately, from the oligomers A and B (lanes v and vi))

Example 3

FIG. 17 shows the melting profiles of $(A.B)_2$, and of the parallel quadruplex, $A_4$, at low concentrations of DNA in a low-salt buffer (TE+100 mM NaCl). $(A.B)_2$ and $A_4$ were first generated by incubation of A.B and, separately, A, in TE+1 M NaCl under conditions of high DNA concentration (~50 $\mu M$ in each case). The solutions were then diluted with ice-cold TE buffer to give stocks with ~50 $\mu M$ DNA in TE+100 mM NaCl. Individual 5 $\mu l$ aliquots from the stock were subjected to ten minute incubations at one of the following temperatures: 20° C., 40° C., 60° C., 80° C. or 100° C., in a thermal cycler pre-set to these individual temperatures. The samples were then chilled on ice and analyzed in a non-denaturing gel (the experiments were carried out a low salt and at low concentrations of DNA to ensure that melted complexes did not renature back to the starting complexes $(A.B)_2$ and $A_4$ within the timescale of the experiment). It can be seen from FIG. 17 that there is a gross difference in the thermal stabilities of the two complexes, with $(A.B)_2$ melting between 40° C. and 60° C., whereas $A_4$ is stable to above 80° C. It has been recognized that parallel quadruplexes are thermodynamically more stable than antiparallel quadruplexes, such as $(A.B)_2$. Melting of $(A.B)_2$ in the more physiological TKMg buffer (data not shown) occurred at ~85° C., indicating the fundamental stability of this complex-dimer under physiological conditions.

Example 4

The question of how many of the eight potential G—G base-pairs in A.B and in A'.B' actually participated in G-quartet formation in $(A.B)_2$ and $(A'.B')_2$ was probed by methylation protection. Guanine bases bonded in quartets are fully protected from methylation; however, in a G—G Hoogsteen base-pair, one of the two guanine bases is expected to be reactive. FIGS. 18a and 18b show methylation protection patterns, carried out in the absence of magnesium, and with the strands A and A' labelled in their respective complexes, of A', A'$_4$, A'. B' and (A'. B')$_2$, FIG. 18a, and the corresponding complexes containing A and B, FIG. 18b. The inner six guanine bases in $(A'.B')_2$ and the inner four of $(A.B)_2$ appear to be protected and, hence, participants in G-quartet formation. These patterns further distinguish these synapsed complexes from parallel quadruplexes ($A_4$ and A'$_4$), in which all but the 5'-most guanine bases are fully protected.

While the present invention has been described with particularity, it should be understood that various modifications and alterations may be made therein without departing from the spirit and scope of the invention set forth in the appended claims.

REFERENCES

1. Amato, I. (1993) *Science* 260, 753–755.
2. Arkin, M. R., Stemp, E. D. A., Holmlin, R. E., Barton, J. K., Hoermann, A., Olson, E. J. C., Barbara, P. F. (1996) *Science* 273, 475–480.
3. Chen, F. M. (1995) *Journal of Biological Chemistry* 270, 23090–23096.
4. Chen, J. H. & Seeman, N. C. (1991) *Nature* 350, 631–633.
5. Duckett, D. R et al., (1988) *Cell* 55, 79–89.
6. Duckett, D. R., & Lilley, D. M. J. (1990) *EMBO J.* 9, 1659–1664.
7. Lu, M., Guo, Q., & Kallenbach, N. (1992) *Biochemistry* 31, 2455–2459.
8. Marsh, T. C. & Henderson, E. (1994) *Biochemsitry* 33, 10718–10724.
9. Marsh, T. C., Vesenka, J., & Henderson, E. (1995) *Nucleic Acids Research* 23, 696–700.
10. Murphy, C. J., et al. (1993) *Science* 262, 1025 .
11. Murphy, C. J., et al. (1994) *Proc. Natl. Acad. Sci. USA* 91, 5315–5319.
12. Seeman, N. C. (1991) *DNA & Cell Biology* 10, 475–486.
13. Seeman, N. C., Zhang, Y., & Chen, J. (1994) *Journal Vacuum Science and Technology* 12(4), 1895–1903.
14. Sen, D. & Gilbert, W. (1991) *Current Opinion in Structural Biology* 1, 435–438.
15. Sen, D. & Gilbert, W. (1992) *Biochemistry* 32, 622–6228.
16. Venczel, E. A. & Sen, D. (1993) *Biochemistry* 32, 6220–6228.
17. Venczel, E. A. & Sen, D. (1996) *Journal of Molecular Biology* 257, 219–224.
18. Wang, Y. L., Mueller, E., Kemper, B., and Seeman, N. C, (1991) *Biochemistry* 30, 5667–5674

We claim:

1. A double-stranded nucleic acid complex, comprising
   a) a plurality of individual strands of nucleic acids, each strand bound antiparallel to another of said strands, along substantially their entire length, to form paired strands in the form of double helices;

b) at least one Watson-Crick domain on said paired strands, said Watson-Crick domain being a region of a least one bound base-pair of said paired strands wherein within each said Watson-Crick domain, each Watson-Crick base on a first strand of said paired strands is bound to a complementary Watson-Crick base on a second strand of said paired strands; and c) at least one guanine domain on said paired strands, said guanine domain being a region of bound guanine pairs of said paired strands wherein within each said guanine domain, a guanine sequence of substantially contiguous guanines on said first strand of said paired strands, is bound to a guanine sequence of substantially contiguous guanines on said second strand of said paired strands to form said guanine domain.

2. A double-stranded nucleic acid complex, comprising a) at least one individual strand of nucleic acid, wherein said strand is folded to form three or more arms of double helices, each of said arms is formed by binding two portions of said strand oriented as to be antiparallel, and b) at least one Watson-Crick domain on each of said arms of said strand wherein each Watson-Crick base on a portion of said strand of said arm binds with another complementary Watson-Crick base on another portion of said strand of said arm, and c) at least one guanine domain of substantially contiguous guanines on each of said arms of said strand wherein guanines on a portion of said strand of said arm bind with guanines on another portion of said strand of said arm.

3. A double-stranded nucleic acid complex according to claim 1, wherein said guanine domain optimally comprises two to eight pairs of said bound guanines.

4. A double-stranded nucleic acid complex according to claim 1 wherein at least one of said strands includes at least one of said guanine domains antiparallel to said Watson Crick domains on one of said strands.

5. A double-stranded nucleic acid complex according to claim 1, wherein at least one of said strands includes at least one of said guanine domains parallel to said Watson-Crick domains on one of said strands.

6. A double-stranded nucleic acid complex according to claim 1, wherein said nucleic acid complex comprises deoxyribonucleic acid.

7. A double-stranded nucleic acid complex according to claim 1, wherein said nucleic acid complex comprises ribonucleic acid.

8. A double-stranded nucleic acid complex according to claim 1, wherein said nucleic acid complex comprises deoxyribonucleic acid and ribonucleic acid.

9. A double-stranded nucleic acid complex according to claim 1, wherein at least one cytosine on said strands is methylated.

10. A double-stranded nucleic acid complex according to claim 1, wherein at least one chemical tag comprising a chemical functionality that is not a natural component of deoxyribonucleic acid or ribonucleic acid and is bound within at least one of said guanine domains thereby conferring specificity to said guanine domain.

11. A double-stranded nucleic acid complex according to claim 10, wherein one of said chemical tags specifically binds to another of said chemical tags.

12. A double-stranded nucleic acid complex according to claim 1, wherein an end of one of said strands is connected to another end of another of said strands with a covalent bond.

13. A double-stranded nucleic acid complex according to claim 1, wherein said end of one of said strands is connected to another end of another of said strands with a chemical linker.

14. A double-stranded nucleic acid complex according to claim 1, wherein said end of one of said strands is connected to another end of another of said strands with a polyether bridge.

15. A double stranded nucleic acid complex according to claim 1, wherein at least one of said guanine domains is adjacent to a substantially contiguous sequence of nucleotides that act as a buffer.

16. A double-stranded nucleic acid complex according to claim 2, wherein said guanine domain optimally comprises two to eight pairs of said bound guanines.

17. A double-stranded nucleic acid complex according to claim 2 wherein at least one of said strands includes at least one of said guanine domains antiparallel to said Watson Crick domains on one of said strands.

18. A double-stranded nucleic acid complex according to claim 2, wherein at least one of said strands includes at least one of said guanine domains parallel to said Watson-Crick domains on one of said strands.

19. A double-stranded nucleic acid complex according to claim 2, wherein said nucleic acid complex comprises deoxyribonucleic acid.

20. A double-stranded nucleic acid complex according to claim 2, wherein said nucleic acid complex comprises ribonucleic acid.

21. A double-stranded nucleic acid complex according to claim 2, wherein said nucleic acid complex comprises deoxyribonucleic acid and ribonucleic acid.

22. A double-stranded nucleic acid complex according to claim 2, wherein at least one cytosine on said strands is methylated.

23. A double-stranded nucleic acid complex according to claim 2, wherein at least one chemical tag comprising a chemical functionality that is not a natural component of deoxyribonucleic acid or ribonucleic acid and is bound within at least one of said guanine domains thereby conferring specificity to said guanine domain.

24. A double stranded nucleic acid complex according to claim 23, wherein one of said chemical tags specifically binds to another of said chemical tags.

25. A double-stranded nucleic acid complex according to claim 2, wherein an end of one of said strands is connected to another end of another of said strands with a covalent bond.

26. A double-stranded nucleic acid complex according to claim 2. wherein said end of one of said strands is connected to another end of another of said strands with a chemical linker.

27. A double-stranded nucleic acid complex according to claim 2, wherein said end of one of said strands is connected to another end of another of said strands with a polyether bridge.

28. A double stranded nucleic acid complex according to claim 1, wherein at least one of said guanine domains is adjacent to a sequence of nucleotides that act as a buffer.

29. A nucleic acid superstructure comprising a plurality of double-stranded nucleic acid complexes according to claim 1 wherein at least one of said guanine domains on one of said double-stranded nucleic acid complexes binds with another of said guanine domains on another of said double-stranded nucleic acid complexes.

30. A nucleic acid superstructure comprising a plurality of double-stranded nucleic acid complexes according to claim 2 wherein at least one of said guanine domains of one of said arms of one of said double-stranded nucleic acid complexes binds with another of said guanine domains of another of said arms of another of said double-stranded nucleic acid complexes.

31. A nucleic acid superstructure according to claim 29, wherein said nucleic acid complexes comprises deoxyribonucleic acid.

32. A nucleic acid superstructure according to claim 29, wherein said nucleic acid complexes comprises ribonucleic acid.

33. A nucleic acid superstructure according to claim 29, wherein said nucleic acid complexes comprises deoxyribonucleic acid and ribonucleic acid.

34. A nucleic acid superstructure according to claim 29, wherein at least one of said chemical tags is bound to at least one of said double-stranded nucleic acid complexes.

35. A nucleic acid superstructure according to claim 34, wherein one of said chemical tags of one of said double-stranded nucleic acid complexes specifically binds with another of said chemical tags of another of said double-stranded nucleic acid complexes.

36. A nucleic acid superstructure according to claim 29, wherein there are a plurality of said guanine domains on a plurality of said double-stranded nucleic acid complexes.

37. A nucleic acid superstructure according to claim 36, wherein a plurality of said double-stranded nucleic acid complexes binds with a plurality of said double-stranded nucleic acid complexes forming a contiguous network of double-stranded nucleic acid complexes.

38. A nucleic acid superstructure according to claim 37, wherein said network of double-stranded nucleic acid complexes is selectively coated in a conductive material.

39. A method of forming a nucleic acid superstructure according to claim 29 comprising the steps of:
   a) synthesizing single strands of nucleic acids wherein each of said strands has a sequence of substantially contiguous guanines;
   b) incubate said single strands in a near physiological buffer wherein said strands self-associate to form double-stranded nucleic acid complexes;
   c) incubate said double-stranded nucleic acid complexes in a near physiological buffer wherein one of said guanine domains of one of said double-stranded nucleic acid complexes binds with another of said guanine domains of another of said double-stranded nucleic acid complexes thereby forming a nucleic acid superstructure;
   d) purify said nucleic acid superstructures.

40. A method according to claim 39, wherein said single strands of nucleic acids comprises deoxyribonucleic acid.

41. A method according to claim 39, wherein said single strands of nucleic acids comprises ribonucleic acid.

42. A method according to claim 39, wherein said single strands of nucleic acids comprises deoxyribonucleic acid and ribonucleic acid.

43. A method of using said double-stranded nucleic acid complexes according to claim 1 in chromatography to separate specific double-stranded nucleic acid complexes from a mixture of nucleic acids and double stranded nucleic acid complexes comprising:
   a) attaching said double-stranded nucleic acid complexes onto a chromatographic column;
   b) adding a mixture of nucleic acids and said double-stranded nucleic acid complexes to said chromatographic column wherein one of said double-stranded nucleic acid complexes in the mixture specifically binds to another of said double-stranded nucleic acid complexes attached onto the chromatographic column;
   c) eluting said nucleic acids from the chromatographic column with a buffer that does not separate said double-stranded nucleic acid complexes bound to said double-stranded nucleic acid complexes attached onto said chromatographic column;
   d) eluting said double-stranded nucleic acid complexes bound to said double-stranded nucleic acid complexes attached onto said chromatographic column with a buffer that releases said double-stranded nucleic acid complexes bound to said double-stranded nucleic acid complexes attached onto said chromatographic column thereby separating said specific double-stranded nucleic acid complexes from said mixture.

44. A method of using double-stranded nucleic acid complexes according to claim 1 in signal amplification comprising:
   a) a plurality of said double-stranded nucleic acid complexes wherein each of said double-stranded nucleic acid complexes has at least one substrate binding site and at least two of said guanine domains, are added to a mixture containing at least one substrate;
   b) a plurality of said double-stranded nucleic acid complexes wherein each of said double-stranded nucleic acid complexes has at least 3 of said guanine domains and at least one determinant chemical tracer, are added to said mixture;
   c) one of said guanine domains of one of said double-stranded nucleic acid complexes with one of said tracers binds with another of said guanine domains of another of said double-stranded nucleic acid complexes with one of said substrate binding sites;
   d) a plurality of said double-stranded nucleic acid complexes with one of said tracers bind with a plurality of said double-stranded nucleic acid complexes with one of said tracers wherein one of said guanine domains of one of said double-stranded nucleic acid complexes with one of said tracers binds with another of said guanine domains of another of said double-stranded nucleic acid complexes with one of said tracers thereby creating a network of said double-stranded nucleic acid complexes with one of said tracers; and
   e) the presence of the double-stranded nucleic acid complex with a tracer is identified.

45. A nucleic acid superstructure according to claim 30, wherein said nucleic acid complexes comprises deoxyribonucleic acid.

46. A nucleic acid superstructure according to claim 30, wherein said nucleic acid complexes comprises ribonucleic acid.

47. A nucleic acid superstructure according to claim 30, wherein said nucleic acid complexes comprises deoxyribonucleic acid and ribonucleic acid.

48. A nucleic acid superstructure according to claim 30, wherein at least one of said chemical tags is bound to at least one of said double-stranded nucleic acid complexes.

49. A nucleic acid superstructure according to claim 48, wherein one of said chemical tags of one of said double-stranded nucleic acid complexes specifically binds with another of said chemical tags of another of said double-stranded nucleic acid complexes.

50. A nucleic acid superstructure according to claim 30, wherein there are a plurality of said guanine domains on a plurality of said double-stranded nucleic acid complexes.

51. A nucleic acid superstructure according to claim 50, wherein a plurality of said double-stranded nucleic acid complexes binds with a plurality of said double-stranded nucleic acid complexes forming a contiguous network of double-stranded nucleic acid complexes.

52. A nucleic acid superstructure according to claim 51, wherein said network of double-stranded nucleic acid complexes is selectively coated in a conductive material.

53. A method of forming a nucleic acid superstructure according to claim 30 comprising the steps of:
 a) synthesizing single strands of nucleic acids wherein each of said strands has a sequence of substantially contiguous guanines;
 b) incubate said single strands in a near physiological buffer wherein said strands self-associate to form double-stranded nucleic acid complexes;
 c) incubate said double-stranded nucleic acid complexes in a near physiological buffer wherein one of said guanine domains of one of said double-stranded nucleic acid complexes binds with another of said guanine domains of another of said double-stranded nucleic acid complexes thereby forming a nucleic acid superstructure;
 d) purify said nucleic acid superstructures.

54. A method according to claim 53, wherein said single strands of nucleic acids comprises deoxyribonucleic acid.

55. A method according to claim 53, wherein said single strands of nucleic acids comprises ribonucleic acid.

56. A method according to claim 53, wherein said single strands of nucleic acids comprises deoxyribonucleic acid and ribonucleic acid.

57. A method of using said double-stranded nucleic acid complexes according to claim 2 in chromatography to separate specific double-stranded nucleic acid complexes from a mixture of nucleic acids and double stranded nucleic acid complexes comprising:
 a) attaching said double-stranded nucleic acid complexes onto a chromatographic column;
 b) adding a mixture of nucleic acids and said double-stranded nucleic acid complexes to said chromatographic column wherein one of said double-stranded nucleic acid complexes in the mixture specifically binds to another of said double-stranded nucleic acid complexes attached onto the chromatographic column;
 c) eluting said nucleic acids from the chromatographic column with a buffer that does not separate said double-stranded nucleic acid complexes bound to said double-stranded nucleic acid complexes attached onto said chromatographic column;
 d) eluting said double-stranded nucleic acid complexes bound to said double-stranded nucleic acid complexes attached onto said chromatographic column with a buffer that releases said double-stranded nucleic acid complexes bound to said double-stranded nucleic acid complexes attached onto said chromatographic column thereby separating said specific double-stranded nucleic acid complexes from said mixture.

58. A method of using double-stranded nucleic acid complexes according to claim 2 in signal amplification comprising:
 a) a plurality of said double-stranded nucleic acid complexes wherein each of said double-stranded nucleic acid complexes has at least one substrate binding site and at lest two of said guanine domains, are added to a mixture containing at least one substrate;
 b) a plurality of said double-stranded nucleic acid complexes wherein each of said double-stranded nucleic acid complexes has at least 3 of said guanine domains and at least one determinant chemical tracer, are added to said mixture;
 c) one of said guanine domains of one of said double-stranded nucleic acid complexes with one of said tracers binds with another of said guanine domains of another of said double-stranded nucleic acid complexes with one of said substrate binding sites;
 d) a plurality of said double-stranded nucleic acid complexes with one of said tracers bind with a plurality of said double-stranded nucleic acid complexes with one of said tracers wherein one of said guanine domains of one of said double-stranded nucleic acid complexes with one of said tracers binds with another of said guanine domains of another of said double-stranded nucleic acid complexes with one of said tracers thereby creating a network of said double-stranded nucleic acid complexes with one of said tracers; and
 e) the presence of the double-stranded nucleic acid complex with a tracer is identified.

* * * * *